United States Patent [19]
Tsubakihara et al.

[11] Patent Number: 5,840,291
[45] Date of Patent: Nov. 24, 1998

[54] BASE MATERIAL FOR HAIR COSMETICS

[75] Inventors: Misao Tsubakihara; Nana Wakita, both of Osaka; Kazuhiro Kato; Tadanori Nakatsuse, both of Saitama, all of Japan

[73] Assignees: Mandom Corporation; Wako Pure Chemical Industries, Ltd., both of Osaka, Japan

[21] Appl. No.: 949,616

[22] Filed: Oct. 14, 1997

Related U.S. Application Data

[63] Continuation of Ser. No. 722,601, Sep. 27, 1996, abandoned.

[30] Foreign Application Priority Data

Oct. 5, 1995 [JP] Japan .................................. 7-286685

[51] Int. Cl.⁶ .................................................... C08G 77/06
[52] U.S. Cl. .................................. 424/70.12; 424/70.122; 526/194; 526/279
[58] Field of Search ........................... 424/70.12, 70.122; 526/194, 279

[56] References Cited

U.S. PATENT DOCUMENTS

| | | | |
|---|---|---|---|
| 5,023,305 | 6/1991 | Onozuka et al. | 526/194 |
| 5,480,634 | 1/1996 | Hayama et al. | 424/70.12 |
| 5,523,365 | 6/1996 | Geck et al. | 526/194 |

FOREIGN PATENT DOCUMENTS

| | | |
|---|---|---|
| 0 582 152 A2 | 2/1994 | European Pat. Off. . |
| WO 93/23009 | 11/1993 | WIPO . |
| WO 95/03776 | 2/1995 | WIPO . |

*Primary Examiner*—Margaret W. Glass
*Attorney, Agent, or Firm*—Armstrong, Westerman, Hattori, McLeland & Naughton

[57] ABSTRACT

The base material for hair cosmetics of the present invention is, as compared with conventional ones, excellent in moisture resistance, set-holding ability and elasticity and it does not cause flaking and when it applies to hair, natural make-up effect can be given to hair and thus treated hair is flexible and smooth in touch and can smoothly be combed.

5 Claims, No Drawings

BASE MATERIAL FOR HAIR COSMETICS

This application is a continuation of application Ser. No. 08/722,601 filed Sep. 27, 1996, now abandoned.

[BACKGROUND OF THE INVENTION]

The present invention relates to a base materials useful for hair cosmetics such as hair care products and/or hair styling agents, including hair setting material, hair treatment, etc.

Base materials for hair cosmetics required at present are those having excellent curl retention effect, set-holding effect, and elasticity, not causing flaking and giving good make-up effect upon applying to hair.

As the base materials for hair cosmetics, an nonionic and cationic base material using a polymer or copolymer of N-vinyl pyrrolidone (Japanese Patent Publication-Kokoku-No. 4533/1981 and Japanese Patent Publication-Kokai-No. 75911/1984) and an anionic base material using a silicone type copolymer (Japanese Patent Publication-Kokai-Nos. 359912/1992, 25411/1990, 924/1994) have been known.

However, nonionic and cationic base materials generally have such defect as low moisture resistance. Anionic base materials, on the other hand, do not give natural make-up effect, though higher moisture resistance compared with nonionic base materials. In order to cover those defects, thus, mixing of plural kind of base materials has been conducted.

However, no fully satisfied base material for hair cosmetics has been obtained.

The present invention has been established taking the above circumstances into consideration, and its object is to provide a base material for hair cosmetics having excellent moisture resistance, set-holding ability and elasticity, not causing flaking and giving good make-up effect upon applying to hair and to provide a copolymer useful for the base material.

[SUMMARY OF THE INVENTION]

The present invention relates to a base material for hair cosmetics, which comprises a block copolymer comprising 5 to 70 wt % of a polysiloxane segment, 10 to 90 of a monomer moiety of an ethylenically unsaturated carboxylic acid and 80% or less of a monomer moiety of an ethylenically unsaturated carboxylic acid ester.

[DESCRIPTION OF THE PREFERRED EMBODIMENT]

The present inventors have made extensive study for looking for a base material for hair cosmetics which has, as compared with so far known base materials for hair cosmetics, excellent curl retention ability, moisture resistance, set-holding ability and elasticity, not causing flaking and giving good make-up effect upon applying to hair and reached to such finding that the object can be attained by using a block copolymer comprising a polysiloxane segment, a monomer moiety of an ethylenically unsaturated carboxylic acid and a monomer moiety of an ethylenically unsaturated carboxylic acid ester, the said copolymer being able to produce by subjecting an ethylenically unsaturated carboxylic acid and an ethylenically unsaturated carboxylic acid ester to polymerization reaction in the presence of a polysiloxane containing azo group(s). On the basis of this finding, the present invention has been completed.

An amount of the polysiloxane segment in the block copolymer is generally 5 to 70 wt %, preferably 7 to 50 wt %, more preferably 20 to 40 wt %. An amount of the moiety of the ethylenically unsaturated carboxylic acid is generally 10 to 90 wt %, preferably 20 to 90 wt %, more preferably 50 to 80 wt %. An amount of the moiety of the ethylenically unsaturated carboxylic acid ester is generally 80 wt % or less, preferably 10 to 70 wt %, more preferably 10 to 50 wt %. The molecular weight of the present block copolymer is, in the number-average one, 10,000 or more, preferably 60,000 to 150,000, more preferably 70,000 to 120,000.

The polysiloxane segment is one having a repeating unit shown by the general formula:

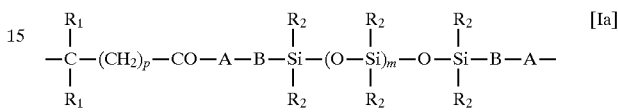

(wherein $R_1$ is, same or different, a hydrogen atom, a lower alkyl or a cyano, $R_2$ is, same or different, a hydrogen atom, an alkyl, a haloalkyl or an aryl, A is NH or O, B is a lower alkylene whose binding may be through one or more oxygen atoms, p is 0 or an integer of 1 to 6 and m is 0 or an integer of 1 to 200) or one having a combination of repeating unit shown by the general formula:

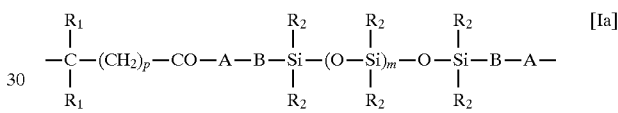

(wherein the symbols have the same meanings as above) and a repeating unit shown by the general formula:

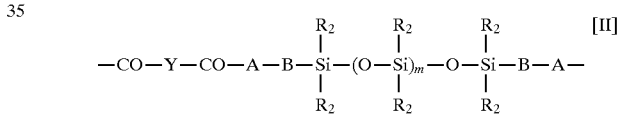

(wherein —CO—Y—CO— is a residue of a dibasic carboxylic acid and other symbols have the same meanings as above).

When an azo-containing polysiloxane having a combination of the repeating unit shown by the general formula [Ia] and one shown by the general formula [II] is used, a ratio of the repeating unit shown by the general formula [Ia] is up to such one as deactivating the radical polymerization activity of the said azo-containing polysiloxane, and the ratio of the former/the latter is generally 70 wt %/30 wt % to 50 wt %/50 wt %.

The monomer moiety of an ethylenically unsaturated carboxylic acid is one having a repeating unit shown by the general formula:

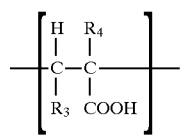

(wherein $R_3$ is a hydrogen atom, a lower alkyl or a carboxyl and $R_4$ is a hydrogen atom, a lower alkyl or a lower carboxyalkyl), and the monomer moiety of an ethylenically unsaturated carboxylic acid ester is one having a repeating unit shown by the general formula:

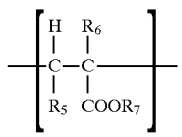

(wherein $R_5$ is a hydrogen atom, a lower alkyl or an alkyloxycarbonyl and $R_6$ is a hydrogen atom, a lower alkyl, a lower carboxyalkyl or an alkyloxycarbonylalkyl, and $R_7$ is an alkyl).

The present block copolymer can schematically be shown by the following general formulas [1] to [3] or any combination of 2 or 3 thereof, even though polymer compounds have generally complex structures and it is difficult to show them accurately.

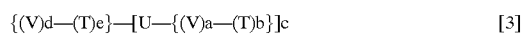

[wherein U is polysiloxane segment, V is the monomer moiety of an ethylenically unsaturated carboxylic acid, T is the monomer moiety of an ethylenically unsaturated carboxylic acid ester, and a, c and d are natural number, b and e are 0 or natural number, [ ] means random structure, including, for example, graft, block and other copolymerization structures].

The block copolymer of present invention is obtained by subjecting an ethylenically unsaturated carboxylic acid of the general formula:

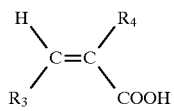

(wherein $R_3$ and $R_4$ have the same meanings as above) and an ethylenically unsaturated carboxylic acid ester of the general formula:

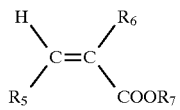

(wherein $R_5$, $R_6$ and $R_7$ have the same meanings as above) to polymerization reaction in the presence of an azo-containing polysiloxane having a repeating unit of the general formula:

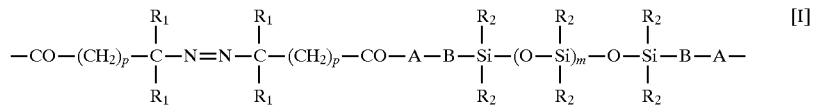

(wherein the symbols have the same meanings as above) or an azo-containing polysiloxane having a combination of a repeating unit of the above general formula [I] and a repeating unit of the general formula:

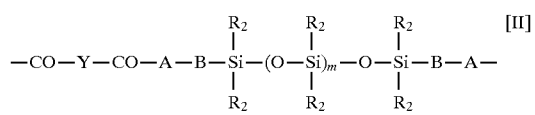

(wherein the symbols have the same meanings as above).

When the azo-containing polysiloxane compound has the combination of the repeating units of the formulas [I] and [II], the ratio of [I]/[II] is 70 wt %/30 wt % to 50 wt %/50 wt %.

The alkyl shown by $R_1$ in the general formulas [I] and [Ia], which may be branched or straight chained, is exemplified by one having 1 to 6 carbon atoms, including specifically methyl, ethyl, n-propyl, isopropyl, n-butyl, isobutyl, tert-butyl, sec-butyl, pentyl, isopentyl, tert-pentyl, 1-methyl pentyl, n-hexyl, isohexyl, and so on. The alkyl shown by $R_2$ in the general formulas [I], [Ia] and [II], which may be branched or straight chained, is exemplified by one having 1 to 20 carbon atoms, including specifically methyl, ethyl, n-propyl, isopropyl, n-butyl, isobutyl, tert-butyl, sec-butyl, pentyl, isopentyl, tert-pentyl, 1-methyl pentyl, n-hexyl, isohexyl, heptyl, octyl, nonyl, decyl, undecyl, dodecyl, hexadexyl, octadecyl, etc. The haloalkyl is exemplified by halogenated (e.g. chlorinated, brominated, fluorinated or iodinated) alkyl having 1 to 20 carbon atoms, including specifically chloromethyl, bromomethyl, trifluoromethyl, 2-chloroethyl, 3-chloropropyl, 3-bromopropyl, 3,3,3-trifluoropropyl, 2-perfluorooctylethyl, etc. The aryl is exemplified by phenyl, tolyl, xylyl, naphthyl, anthryl, etc. A lower alkylene moiety of the lower alkylene shown by B, whose binding may be through one or more oxygen atoms, preferably 1 to 5, more preferably 1 to 3, is exemplified by one having 1 to 6 carbon atoms, including specifically methylene, ethylene, trimethylene, tetramethylene, pentamethylene, hexamethylene, —$CH_2$—O—$CH_2$—, —$CH_2CH_2$—O—$CH_2$—, —$CH_2CH_2$—O—$CH_2CH_2$—, —$CH_2CH_2$—O—$CH_2CH_2$—O—$CH_2CH_2$— etc. The dibasic acid residue shown by —CO—Y—CO— is exemplified by residues of malonic acid, succinic acid, glutaric acid, adipic acid, sebacic acid, phthalic acid, isophthalic acid, terephthalic acid, pimelic acid, suberic acid, azelaic acid, fumaric acid, maleic acid, itaconic acid, malic acid, 1,4-naphthalene dicarboxylic acid, 4,4-biphenyl dicarboxlic acid, etc.

The lower alkyl shown by $R_3$ and $R_4$ in the general formula [III], which may be branched or straight chained, is exemplified by one having 1 to 6 carbon atoms, including specifically methyl, ethyl, n-propyl, isopropyl, n-butyl, isobutyl, tert-butyl, sec-butyl, pentyl, isopentyl, tert-pentyl, 1-methyl pentyl, n-hexyl, isohexyl, etc. The lower carboxyalkyl shown by $R_4$ is exemplified by those alkyls mentioned above whose hydrogen atom(s) are substituted by carboxyl group, including specifically carboxymethyl, carboxyethyl, carboxypropyl, carboxybutyl, carboxypentyl, carboxyhexyl, etc.

The ethylenically unsaturated carboxylic acid of the general formula [III] is exemplified by, but not limited to, acrylic acid, methacrylic acid, itaconic acid, maleic acid, fumaric acid, crotonic acid, citraconic acid, mesaconic acid, etc., and those acids may form their salts such as alkali metal (e.g. Li, Na, K) and ammonium salts.

The lower alkyl shown by $R_5$ and $R_6$ in the general formula [IV], which may be branched or straight chained, is exemplified by one having 1 to 6 carbon atoms, including specifically methyl, ethyl, n-propyl, isopropyl, n-butyl, isobutyl, tert-butyl, sec-butyl, pentyl, isopentyl, tert-pentyl, 1-methyl pentyl, n-hexyl, isohexyl, etc. The an alkyloxycarbonyl shown by $R_5$ is exemplified by one having 2 to 7 carbon atoms, including specifically methyloxycarbonyl, ethyloxycarbonyl, propyloxycarbonyl, butyloxycarbonyl, pentyloxycarbonyl, hexyloxycarbonyl, etc. The lower carboxyalkyl shown by $R_6$ is exemplified by those alkyls mentioned above whose hydrogen atom(s) are substituted by carboxyl, including specifically carboxymethyl, carboxyethyl, carboxypropyl, carboxybutyl, carboxypentyl, carboxyhexyl, etc. The alkyloxycarbonylalkyl shown by $R_6$ is exemplified by those carboxyalkyls mentioned above whose carboxyl is esterified by alkyl, including specifically methyloxycarbonylmethyl, methyloxycarbonylethyl, ethyloxycarbonylmethyl, ethyloxycarbonylethyl, propyloxycarbonylmethyl, propyloxycarbonylethyl, butyloxycarbonylmethyl, butyloxycarbonylethyl, pentyloxycarbonylmethyl, pentyloxycarbonylethyl, hexyloxycarbonylmethyl, hexyloxycarbonylethyl, etc. The alkyl shown by $R_7$, which may be branched or straight chained, is exemplified by one having 1 to 20 carbon atoms, including specifically methyl, ethyl, propyl, butyl, pentyl, hexyl, heptyl, octyl, nonyl, decyl, undecyl, dodecyl, hexadecyl, octadecyl, etc.

The ethylenically unsaturated carboxylic acid ester shown by the general formula [IV] is exemplified by, but not limited to, methyl methacrylate, ethyl methacrylate, propyl methacrylate, tert-butyl methacrylate, n-butyl methacrylate, isobutyl methacrylate, 2-ethyl hexyl methacrylate, lauryl methacrylate, stearyl methacrylate, methyl itaconate, ethyl itaconate, methyl maleate, ethyl maleate, methyl fumarate, ethyl fumarate, methyl crotonate, ethyl crotonate, etc.

The molecular weight of the copolymer of the present invention is not specifically limited, and generally the copolymer having a number-average molecular weight of 10,000 or more is advantageously used because too small molecular weight of the copolymer causes problem on moisture resistance. Thus, a number-average molecular weight is selected from 60,000 to 150,000, preferably 70,000 to 120,000.

The azo-containing polysiloxane used in production of the copolymer of the present invention is one having a number-average molecular weight of generally 1,500 to 200,000, preferably 3,000 to 150,000.

The ratio of the polysiloxane moiety in the copolymer of the present invention is not specifically limited but too small ratio causes bad effect to touch and feeling and too much ratio causes decrease in solubility, and thus the ratio is preferably selected from a range of 5 to 70 wt %, preferably 7 to 50 wt %, more preferably 20 to 40 wt %.

The ratio of the ethylenically unsaturated carboxylic acid moiety in the copolymer is not specifically limited but too small ratio results in such problems as decrease in moisture resistance, decrease in compatibility and adhesion to hair and decrease in solubility in water, alcohol and other solvents, so that removal of the conditioner becomes difficult, and on the other hand, too much ratio results in lowering the relative content of the azo-containing polysiloxane so that such defect as lowering water-repellent effect by the siloxane is observed, and thus the ratio is selected from 10 to 90 wt %, preferably a range of 20 to 90 wt %, more preferably 50 to 80 wt %.

As to the ratio of the ethylenically unsaturated carboxylic acid ester moiety of the copolymer, too much ratio causes decrease in sliding effect on the surface of hair and too much ratio results in lowering the relative contents of the azo-containing polysiloxane and the ethylenically unsaturated carboxylic acid so that moisture resistance is decreased, and thus the ratio is selected from less than 80 wt %, preferably 10 to 70 wt %, more preferably 10 to 50 wt %.

The azo-containing polysiloxane of the present invention having the repeating unit shown by the general formula [I] can easily be produced, for example, by the method disclosed in a Japanese Patent Publication-Kokai-No. 372675/1992.

Namely, the polysiloxane can be produced by reacting a diamine or diol compound containing a polysiloxane segment shown by the general formula:

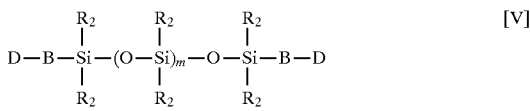

(wherein D is $NH_2$ or OH and $R_2$, B and m have the same meanings as above) with an azo-containing dibasic acid dihalide shown by the general formula:

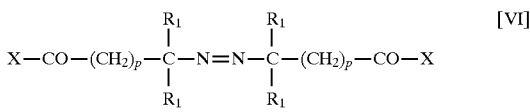

(wherein $R_1$ and p have the same meanings as above, and X is a halogen atom) in the presence of a basic catalyst in a suitable solvent.

The azo-containing polysiloxane compound of the present invention having the repeating unit shown by the general formula [I] may be produced also by a method disclosed in a Japanese Patent Publication-Kokai-No. 93100/1994 or 322089/1994.

Namely, the compound can be produced by reacting a diamine or diol compound containing a polysiloxane segment shown by the general formula [V] with an azo-containing dibasic acid shown by the general formula:

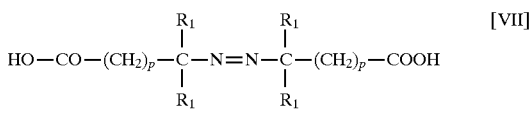

(wherein $R_1$ and p have the same meanings as above) in the presence of a basic catalyst and dehydrating condensing agent in a suitable solvent.

The above preparation methods can advantageously be conducted in the presence of a basic catalyst, and the basic catalyst is exemplified by an organic amine such as triethylamine, N,N-dimethylaniline, piperidine, pyridine, 4-dimethylaminopyridine, 1,5-diazabicyclo[4,3,0]non-5-ene, 1,8-diazabicyclo[5,4,0]undec-7-ene and tri-n-butylamine and an alkaline metal compound such as sodium hydride and n-butyl lithium. In the latter method, a dehydrating condensing agent is used, and the agent is exemplified by polyphosphoric acid, dicyclohexylcarbodiimide, diisopropylcarbodiimide, 1-ethyl-3-(3-dimethylaminopropylcarbodiimide)hydrochloride, carbonyl diimidazol and p-toluenesulfonyl chloride.

The reaction solvent is exemplified by an ether such as diethyl ether, diisopropyl ether, tetrahydrofuran, dioxane, and dimethoxy ethane, a halogenated hydrocarbon such as carbon tetrachloride, chloroform, methylene chloride, 1,2-dichloroethane and trichloroethylene, an ester such as ethyl acetate, butyl acetate and methyl propionate, acetonitrile, N,N-dimethyl formamide, etc. The solvent may be used alone or in combination of two or more ones.

The ratio of the diamine or diol compound shown by the general formula [V] and the azo-containing dibasic acid dihalide shown by the general formula [VI] or the azo-containing dibasic acid shown by the general formula [VII] to be used can suitably be selected without any specific limitation, but in order to obtain the azo-containing polysiloxane having high molecular weight, the both compounds are used preferably in about equimolar ratio.

The amount of the dehydrating condensing agent to be used is not specifically limited, but when the amount is too small, the reaction speed is decreased and when the amount is too large, the control of the molecular weight is difficult, and not economic, though high molecular weight compound can be produced in short reaction period of time, and thus the amount is selected generally from 1 to 5 times mole parts, preferably 2 to 3 times mole parts, relative to the corresponding diamine or diol compound. The amount of the basic catalyst to be used is selected generally from 0.5 to 5 times mole parts, preferably 0.5 to 1.5 times mole parts, relative to the starting compound shown by the general formula [VI] or [VII] or relative to the dehydrating condensing agent.

The reaction temperature is not specifically limited, but when the temperature is too high, the azo groups are decomposed, and when the temperature is too low, the reaction becomes slow to require long reaction time and further it becomes difficult to obtain the azo-containing polysiloxane having high molecular weight, and thus it is suitably selected from −10° to 60° C. It may also be possible to increase the reaction temperature gradually. The reaction time to be required is different according to the reaction method and generally selected from 1 to 60 hours.

The isolation of the objective compound can be conducted by suitably depending upon the kind and the amount of the starting materials, basic catalyst, dehydrating condensing agent and solvent which are used in the reaction, and also upon the state of the reaction solution. For instance, when the reaction solution is viscous, the solution is diluted with a suitable solvent, then impurities such as quaternary ammonium salt by-produced are removed by filtration or washing with water, and then the solvent is removed, whereby the objective azo-containing polysiloxane compound can be obtained.

When the azo-containing polysiloxane compound having the combination of the repeating unit shown by the general formula [I] and the repeating unit shown by the general formula [II] is to be produced, the same reaction as mentioned above is conducted with the use of a mixture of the azo-containing dibasic acid dihalide shown by the general formula [VI] and such a compound wherein a part of the said dihalide is substituted by a dibasic acid dihalide of the formula X—OC—Y—CO—X (X has the same meaning as above) or a mixture of the azo-containing dibasic acid shown by the general formula [VI] and such a compound wherein a part of the dibasic acid is substituted by a dibasic acid of the formula HOOC—Y—COOH.

The copolymer of the present invention can be produced as follows.

Namely, the azo-containing polysiloxane compound obtained above is subjected to polymerization reaction with the ethylenically unsaturated carboxylic acid and ethylenically unsaturated carboxylic acid ester in a suitable solvent under inert gas atmosphere according to a conventional manner.

Treatment after the polymerization reaction can be conducted according to a conventional manner so far used in this kind of technical field.

The molecular weight may be controlled, if desired, by using a chain-transfer agent such as lauryl mercaptan, octyl mercaptan, butyl mercaptan, 2-mercaptoethanol and butyl thioglycolate upon conducting the polymerization reaction.

Any azo-containing polysiloxane compound can be used in the polymerization reaction so far as it has at least one azo group per molecule, but when the average molecular weight of the compound is low, remarkable amount of the compound having no azo group co-exists and thus the yield of the objective block copolymer to be produced becomes low, which means that the function of the compound cannot be effected, and when the average molecular weight is too high, on the other hand, a long reaction time is required and further solubility is decreased and viscosity of the reaction solution is increased so that the block copolymerization reaction has to be conducted in a low concentration of the reactants, which results in such defects as lowering the polymerization degree with the ethylenically unsaturated carboxylic acid and carboxylic acid ester. Thus, the number-average molecular weight of the compound is generally selected from 1,500 to 200,000, preferably 3,000 to 150,000.

The amount of the azo-containing polysiloxane to be used upon the polymerization reaction is selected from generally 5 to 70 wt %, preferably 5 to 65 wt %, more preferably 10 to 65 wt %.

The amount of the ethylenically unsaturated carboxylic acid to be used in the polymerization reaction is selected from generally 10 to 80 wt %, preferably 15 to 80 wt %, more preferably 20 to 75 wt %.

The amount of the ethylenically unsaturated carboxylic acid ester to be used in the polymerization reaction is selected from generally less than 80 wt %, preferably 10 to 70 wt %, more preferably 15 to 70 wt %.

The polymerization reaction is conducted preferably in the presence of an organic solvent. The organic solvent is exemplified by a hydrocarbon such as toluene, xylene, benzene, cyclohexane, n-hexane and n-octane, a halogenated hydrocarbon such as 1,2-dichloroethane and trichloroethane, an ester such as ethyl acetate, n-butyl acetate and methyl propionate, a ketone such as acetone, methyl ethyl ketone and cyclohexanone, an alcohol such as methanol, ethanol, n-propanol, isopropanol, n-butanol, isobutanol and tert-butanol, N-methyl pyrrolidone, N,N-dimethyl acetamide, dimethyl sulfoxide, etc., among which ethanol and isopropanol are preferable.

The inert gas includes nitrogen gas, argon gas, etc.

The polymerization temperature is not specifically limited, but when the temperature is too low, degree of decomposition of the azo group is low so that polymerization speed becomes low, and when the temperature is too high, too much decomposition of the azo groups occurs so that control of polymerization becomes difficult.

Thus, the polymerization temperature is selected from generally 20° to 150° C., preferably 40° to 120° C. The polymerization reaction time varies depending upon the kind and amount of the azo-containing polysiloxane compound, the ethylenically unsaturated carboxylic acid and the ethylenically unsaturated carboxylic acid ester and also the concentration of those materials in the reaction, and generally selected from 2 to 24 hours.

When the copolymer thus obtained is used as the base material for hair cosmetics, the copolymer is generally put into use in the state of a solution obtained by dissolving in water and/or a hydrophilic organic solvent, and the copolymer is preferably neutralized by a basic substance so as to make it water-soluble.

The basic substance to be used for the neutralization is exemplified by an alkaline metal hydroxide, an alkaline earth metal hydroxide, an aqueous ammonium solution, an organic amine including monoethanol amine, diethanol amine, triethanol amine, monoisopropanol amine, diisopropanol amine, triisopropanol amine, 2-amino-2-methylpropanol, 3-amino-2-methylpropanol, 2-amino-2-methylpropan-1,3-diol, morpholine, etc.

The degree of the neutralization is selected from generally 30 to 100%, preferably 50 to 100%.

The hydrophilic organic solvent to be used for dissolving the copolymer for the use as a base material for hair cosmetics includes various kind of lower alcohols and glymes, among which ethanol and isopropanol and the like are mentioned as preferable ones from view point of affect to human body.

The base material for hair cosmetics, which comprises the block copolymer of the present invention is excellent in solubility in water and ethanol, and is also excellent in characteristics necessary for the base material for hair cosmetics, such as set-holding ability, moisture resistance, elasticity, anti-flaking ability, touch and feeling, and the like, and also excellent in make-up effect upon applying to hair, and thus the material is extraordinary useful for a setting agent, a treatment agent, and so on, and it is put into use in the state of mousse, jel, lotion, spraying, cream, and the like.

When the copolymer of the present invention is used as the base material for hair cosmetics, other cosmetic components can be incorporated therewith, so far as degrading the function of the material. The components usable include a surfactant such as an anionic surfactant, cationic surfactant, nonionic surfactant and amphoteric surfactant, an oily substance such as oil and fat, an ester oil, a hydrocarbon, wax, a wax ester, a silicone or its derivative, a fluorine compound or its derivative, a higher fatty acid and a higher alcohol, a polymer such as an anionic polymer, a cationic polymer, a nonionic polymer and an amphoteric polymer, a sugar and a polysaccharide and their derivative, an inorganic or organic acid, a base, a buffering agent, a salt, a solvent such as water and a lower alcohol, liquified gas such as liquified petroleum gas (LPG), dimethyl ether (DME) and flon, a propellant such as compressed carbon dioxide gas and compressed nitrogen gas, and also other ones such as a protein derivative, an extract of a crude drug and other plants, an essential oil, an anti-fungi and anti-bacterial agent, an anti-oxidant, an UV-absorber, a metal ion-blocking agent, an oxidant, a reducing agent, a coloring agent, a perfume, etc.

In the following, the present invention is further explained with citation of examples and reference examples, but the present invention is not limited those examples.

[EXAMPLES]

Reference Example 1

3.5 Grams of 4-dimethylamino pyridine (hereinafter abbreviated as DMAP) and 8.0 g of 4,4'-azobis(4-cyanopentanoic acid) are dissolved in 160 ml of methylene chloride, and then 125 g of an amino-modified silicone KF-8012 [the compound shown by the above general formula (V) wherein $R_2$ is methyl, D is amino, B is $(CH_2)_3$ and m is about 56 in average; Trade Name of the product of Sin-Etsu Silicone Co., Ltd.] and 13.0 g of dicyclohexylcarbodiimide (hereinafter abbreviated as DCC) are added in this order to the resultant, followed by allowing a reaction to take place at 20° to 30° C. for 4 hours with agitation. The resultant is diluted with 160 ml of methylene chloride, and water and methanol are added thereto to cease the reaction. The resulting precipitates are removed by filtration, and the filtrate is poured into a large amount of methanol to precipitate the objective substance. The supernatant is removed and the residue is dried under reduced pressure at room temperature to give 103 g of the objective product. The product is confirmed as an azo-containing polysiloxane amide containing polysiloxane segments by $^1H$ —NMR spectrum and infrared spectrum. The number-average molecular weight of the polysiloxane is 20,000 by GPC analysis, and an average azo-binding number is 4.3. This product is hereinafter referred to as MAI-1.

Reference Example 2

33.7 Grams of DMAP and 77.3 g of 4,4'-azobis(4-cyanopentanoic acid) are dissolved in 2500 ml of methylene chloride, and then 1214 g of an amino-modified silicone KF-8012 [the compound shown by the above general formula (V) wherein $R_2$ is methyl, D is amino, B is $(CH_2)_3$ and m is about 56 in average; Trade Name of the product of Sin-Etsu Silicone Co., Ltd.] and 125 g of DCC are added in this order to the resultant, followed by allowing a reaction to take place at 20° to 30° C. for 7 hours with agitation. Then water and methanol are added thereto to cease the reaction. The resulting precipitates are removed by filtration, and the filtrate is poured into a large amount of methanol to precipitate the objective substance. The supernatant is removed and the residue is dried under reduced pressure at room temperature to give 1070 g of the objective product. The product is confirmed as an azo-containing polysiloxane amide containing polysiloxane segments by $^1H$ —NMR spectrum and infrared spectrum. The number-average molecular weight of the polysiloxane is 30,000 by GPC analysis, and an average azo-binding number is 6.5. This product is hereinafter referred to as MAI-2.

Reference Example 3

3.5 Grams of DMAP and 8.0 g of 4,4'-azobis(4-cyanopentanoic acid) are dissolved in 160 ml of methylene chloride, and then 125 g of an amino-modified silicone KF-8012 [the compound shown by the above general formula (V) wherein $R_2$ is methyl, D is amino, B is $(CH_2)_3$ and m is about 56 in average; Trade Name of the product of Sin-Etsu Silicone Co., Ltd.] and 13.0 g of DCC are added in this order to the resultant, followed by allowing a reaction to take place at 20° to 30° C. for 8 hours with agitation. After keeping standing overnight, the product is diluted with 160 ml of methylene chloride, and then water and methanol are added thereto to cease the reaction. The resulting precipitates are removed by filtration, and the filtrate is poured into a large amount of methanol to precipitate the objective substance. The supernatant is removed and the residue is dried under reduced pressure at room temperature to give 114 g of the objective product. The product is confirmed as an azo-containing polysiloxane amide containing polysiloxane segments by $^1H$ —NMR spectrum and infrared spectrum. The number-average molecular weight of the polysiloxane is 45,000 by GPC analysis, and an average azo-binding number is 9.7. This product is hereinafter referred to as MAI-3.

Reference Example 4

3.5 Grams of DMAP and 8.0 g of 4,4'-azobis(4-cyanopentanoic acid) are dissolved in 160 ml of methylene chloride, and then 325 g of an amino-modified silicone KF-8008 [the compound shown by the above general formula (V) wherein $R_2$ is methyl, D is amino, B is $(CH_2)_3$ and m is about 150 in average; Trade Name of the product of Sin-Etsu Silicone Co., Ltd.] and 13.0 g of DCC are added in this order to the resultant, followed by allowing a reaction to take place at 20° to 30° C. for 5 hours with agitation. The product is diluted with 160 ml of methylene chloride, and then water and methanol are added thereto to cease the reaction. The resulting precipitates are removed by filtration, and the filtrate is poured into a large amount of methanol to precipitate the objective substance. The supernatant is removed and the residue is dried under reduced pressure at room temperature to give 275 g of the objective product. The product is confirmed as an azo-containing polysiloxane amide containing polysiloxane segments by $^1H$ —NMR spectrum and infrared spectrum. The number-average molecular weight of the polysiloxane is 47,000 by GPC analysis, and an average azo-binding number is 4.0. This product is hereinafter referred to as MAI-4.

Reference Example 5

13.2 Grams of DMAP and 30.3 g of 4,4'-azobis(4-cyanopentanoic acid) are dissolved in 540 ml of methylene chloride, and then 1230 g of an amino-modified silicone KF-8008 [the compound shown by the above general formula (V) wherein $R_2$ is methyl, D is amino, B is $(CH_2)_3$ and m is about 150 in average; Trade Name of the product of Sin-Etsu Silicone Co., Ltd.] and 49.8 g of DCC are added in this order to the resultant, followed by allowing a reaction to take place at 20° to 30° C. for 8 hours with agitation. After keeping standing overnight, the product is diluted with 2400 ml of methylene chloride, and then water and methanol are added thereto to cease the reaction. The resulting precipitates are removed by filtration, and the filtrate is poured into a large amount of methanol to precipitate the objective substance. The supernatant is removed and the residue is dried under reduced pressure at room temperature to give 1050 g of the objective product. The product is confirmed as an azo-containing polysiloxane amide containing polysiloxane segments by $^1H$ —NMR spectrum and infrared spectrum. The number-average molecular weight of the polysiloxane is 86,000 by GPC analysis, and an average azo-binding number is 7.4. This product is hereinafter referred to as MAI-5.

Reference Example 6

3.5 Grams of DMAP and 8.0 g of 4,4'-azobis(4-cyanopentanoic acid) are dissolved in 160 ml of methylene chloride, and then 325 g of an amino-modified silicone KF-8008 [the compound shown by the above general formula (V) wherein $R_2$ is methyl, D is amino, B is $(CH_2)_3$ and m is about 150 in average; Trade Name of the product of Sin-Etsu Silicone Co., Ltd.] and 13.0 g of DCC are added in this order to the resultant, followed by allowing a reaction to take place at 20° to 30° C. for 12 hours with agitation. The product is diluted with 160 ml of methylene chloride, and then water and methanol are added thereto to cease the reaction. The resulting precipitates are removed by filtration, and the filtrate is poured into a large amount of methanol to precipitate the objective substance. The supernatant is removed and the residue is dried under reduced pressure at room temperature to give 275 g of the objective product. The product is confirmed as an azo-containing polysiloxane amide containing polysiloxane segments by $^1H$ —NMR spectrum and infrared spectrum. The number-average molecular weight of the polysiloxane is 125,000 by GPC analysis, and an average azo-binding number is 10.7. This product is hereinafter referred to as MAI-6.

Reference Example 7

3.5 Grams of DMAP and 8.0 g of 4,4'-azobis(4-cyanopentanoic acid) are dissolved in 160 ml of methylene chloride, and then 125 g of an amino-modified silicone KF-8012 [the compound shown by the above general formula (V) wherein $R_2$ is methyl, D is amino, B is $(CH_2)_3$ and m is about 56 in average; Trade Name of the product of Sin-Etsu Silicone Co., Ltd.] and 13.0 g of DCC are added in this order to the resultant, followed by allowing a reaction to take place at 20° to 30° C. for 7.5 hours with agitation. The resultant is diluted with 160 ml of methylene chloride, and water and methanol are added thereto to cease the reaction. The resulting precipitates are removed by filtration, and the filtrate is poured into a large amount of methanol to precipitate the objective substance. The supernatant is removed and the residue is dried under reduced pressure at room temperature to give 110 g of the objective product. The product is confirmed as an azo-containing polysiloxane amide containing polysiloxane segments by $^1H$ —NMR spectrum and infrared spectrum. The number-average molecular weight of the polysiloxane is 37,200 by GPC analysis, and an average azo-binding number is 9.5. This product is hereinafter referred to as MAI-7.

Synthesis Example 1

7.5 Grams of MAI-2 obtained in Reference Example 2, 90.0 g of methacrylic acid (hereinafter abbreviated as MAA), 35.7 g of tert-butyl methacrylate (hereinafter abbreviated as BMA) and 540 g of n-propanol are mixed with one another and the mixture is subjected to polymerization reaction under nitrogen gas stream at 80° C. for 6 hours. After the reaction, the reaction solution is poured into n-hexane to precipitate the resulting block copolymer. The block copolymer is recovered by filtration, washed with water and dried under reduced pressure at 80° C. for 6 hours to give 64 g (yield:47%) of the block copolymer. The block copolymer is found as a vinyl-silicone block copolymer having weight ratio of dimethyl siloxane segment (DMS) :MAA:BMA=5.7:63.7:30.6 by NMR analysis and having a number-average molecular weight of 84,000 and a weight-average molecular weight of 129,900 by GPC. The result is shown in Table 1.

Synthesis Examples 2 to 15

The objective vinyl-silicone block copolymers are obtained after the same manner as in Synthesis Example 1 except for the kind and amount of MAI and the amount of MAA, BMA and the solvent which are shown in the Table 1. The result is shown in Table 1.

Synthesis Example 16

20 Grams of MAI-5 obtained in Reference Example 5, 48 g of MAA, 20 g of BMA and 352 g of ethanol are mixed with one another and the mixture is subjected to polymerization reaction under nitrogen gas stream at 77° C. for 3 hours. Then, 0.5 g of dimethyl 2,2'-azobisisobutyrate (Trade Name: V-601; manufactured and sold by Wako Pure Chemical Industries, Ltd.) is added to the resultant, followed by conducting polymerization reaction for further 4 hours. After the reaction, the reaction solution is poured into n-hexane to precipitate the block copolymer. The block copolymer is recovered by filtration, washed with water and dried under reduced pressure at 80° C. for 6 hours to give 62.4 g (yield:70.9%) of the block copolymer. The block copolymer is found as a vinyl-silicone block copolymer having weight ratio of dimethyl siloxane segment (DMS) :MAA:BMA=16.0:53.7:30.3 by NMR analysis and having a number-average molecular weight of 30,000 and a weight-average molecular weight of 94,000 by GPC. The result is shown in Table 1.

Synthesis Example 17

The objective vinyl-silicone block copolymers are obtained after the same manner as in Synthesis Example 16 except for using 282 g of ethanol in place of 352 g of ethanol. The result is shown in Table 1.

Synthesis Examples 18 to 21

The objective vinyl-silicone block copolymers are obtained by the same manner as in Synthesis Example 1 except for using MAI-5 in place of MAI-1, and using methyl methacrylate (Synthesis Example 18), ethyl methacrylate (Synthesis Example 19), 2-ethylhexyl methacrylate (Synthesis Example 20) and stearyl methacrylate (Synthesis Example 21), respectively in place of BMA. The result is shown in Table 2.

Synthesis Example 22

The objective vinyl-silicone block copolymer is obtained by the same manner as in Example 1 except for using acrylic acid and MAI-5 in place of MAA and MAI-2. The result is shown in Table 2.

Synthesis Examples 23 to 28

The objective vinyl-silicone block copolymers are obtained after the same manner as in Synthesis Example 1 except for the kind and amount of MAI, the kind of ethylenically unsaturated carboxylic acid, the ethylenically unsaturated carboxylic acid ester and the solvent which are shown in Table 2. The result is shown in Table 2.

TABLE 1

| Syn. Exp. | MAI | solvent | Amount used (wt %) | | | Component used (wt %) | | | Molecular weight | | | Solubility[1] | | |
|---|---|---|---|---|---|---|---|---|---|---|---|---|---|---|
| | | | MAI | MAA | BMA | DMS | MAA | BMA | Mn | Mw | Mw/Mn | Water[2] | EtOH[3] | Compatibility[4] |
| 1 | MAI-2 | n-PrOH | 5.6 | 67.6 | 26.8 | 5.7 | 63.7 | 30.6 | 84000 | 129900 | 1.55 | good | good | good |
| 2 | MAI-2 | IPA | 10.6 | 63.1 | 26.3 | 8.7 | 61.3 | 30.0 | 53400 | 84700 | 1.62 | good | good | good |
| 3 | MAI-2 | IPA | 26.1 | 52.1 | 21.8 | 22.5 | 52.0 | 25.5 | 30700 | 51400 | 1.67 | good | good | good |
| 4 | MAI-2 | n-PrOH | 37.2 | 44.6 | 18.2 | 31.6 | 42.7 | 25.7 | 30600 | 50600 | 1.65 | good | good | good |
| 5 | MAI-2 | n-PrOH | 35.7 | 53.6 | 10.7 | 31.3 | 54.3 | 14.4 | 29000 | 53000 | 1.84 | good | good | good |
| 6 | MAI-2 | n-PrOH | 50.0 | 50.0 | 0 | 20.6 | 79.4 | 0 | — | — | — | good | good | good |
| 7 | MAI-2 | n-PrOH | 50.0 | 35.3 | 14.7 | 42.9 | 37.0 | 20.1 | 25000 | 49000 | 1.96 | good | good | good |
| 8 | MAI-2 | n-PrOH | 63.9 | 25.5 | 10.6 | 60.0 | 25.3 | 14.7 | 20000 | 43000 | 2.10 | good | good | good |
| 9 | MAI-5 | n-PrOH | 37.0 | 44.5 | 18.5 | 35.6 | 39.8 | 24.6 | 63000 | 102000 | 1.64 | good | good | good |
| 10 | MAI-5 | n-PrOH | 46.9 | 37.5 | 15.6 | 50.7 | 30.3 | 19.0 | 57000 | 96000 | 1.68 | good | good | good |
| 11 | MAI-5 | n-PrOH | 22.8 | 54.5 | 22.7 | 23.0 | 48.0 | 29.0 | 89000 | 139000 | 1.56 | good | good | good |
| 12 | MAI-5 | EtOH | 22.8 | 54.5 | 22.7 | 18.1 | 50.9 | 31.0 | 82000 | 132000 | 1.61 | good | good | good |
| 13 | MAI-5 | EtOH | 22.8 | 54.5 | 22.7 | 18.9 | 49.5 | 31.6 | 73000 | 119000 | 1.63 | good | good | good |
| 14 | MAI-4 | EtOH | 22.8 | 54.5 | 22.7 | 16.4 | 48.6 | 35.0 | 69000 | 128000 | 1.85 | good | good | good |
| 15 | MAI-3 | EtOH | 39.1 | 19.6 | 41.3 | 39.7 | 14.4 | 45.9 | 38400 | 72300 | 1.88 | good | good | good |
| 16 | MAI-5 | EtOH | 22.8 | 54.5 | 22.7 | 16.0 | 53.7 | 30.3 | 30000 | 94000 | 3.13 | good | good | good |
| 17 | MAI-5 | EtOH | 22.8 | 54.5 | 22.7 | 17.8 | 50.1 | 32.1 | 27000 | 103000 | 3.73 | good | good | good |

MAI: azo-containing polysiloxane compound
n-PrOH: 1-propanol
IPA: 2-propanol
EtOH: ethyl alcohol
MAA: methacrylic acid
BMA: t-butyl methacrylate
DMS: dimethyl siloxane
Mn: number-average molecular weight
Mw: weight-average molecular weight
Solubility[1]: Judgement was based on transparency of each solution.
water[2]: 2% aqueous solution of the copolymer which is perfectly neutralized with 2-amino-2-methylpropanol.
EtOH[3]: 2% ethanol solution.
compatibility[4]: 2% water/ethanol(50 w/w/50 w/w) solution of the copolymer which is perfectly neutralized with 2-amino-2-methylpropanol.

TABLE 2

| Syn. Exp. | MAI | solvent | Amount used (wt %) | | | Component used (wt %) | | | Molecular weight | | | Solubility[1] | | |
|---|---|---|---|---|---|---|---|---|---|---|---|---|---|---|
| | | | MAI | ① | ② | DMS | ① | ② | Mn | Mw | Mw/Mn | Water[2] | EtOH[3] | Compatibility[4] |
| 18 | MAI-5 | EtOH | 22.8 | 54.5 | 22.7 | 19.0 | 59.3 | 21.7 | 81000 | 132000 | 1.63 | good | good | good |
| 19 | MAI-5 | EtOH | 22.8 | 54.5 | 22.7 | 21.6 | 54.4 | 24.0 | 79000 | 130000 | 1.66 | good | good | good |
| 20 | MAI-5 | EtOH | 22.8 | 54.5 | 22.7 | 17.8 | 53.7 | 28.5 | 76000 | 137000 | 1.79 | good | good | good |
| 21 | MAI-5 | EtOH | 22.8 | 54.5 | 22.7 | 16.5 | 63.3 | 20.2 | 85000 | 162000 | 1.90 | good | good | good |
| 22 | MAI-5 | EtOH | 22.8 | 54.5 | 22.7 | 9.5 | 54.8 | 35.7 | 11000 | 44000 | 3.91 | good | good | good |
| 23 | MAI-5 | EtOH | 22.7 | 54.6 | 22.7 | 18.3 | 44.0 | 37.7 | 58000 | 99000 | 1.70 | good | good | good |
| 24 | MAI-5 | EtOH | 22.8 | 54.5 | 22.7 | 17.2 | 51.5 | 31.3 | 75000 | 124000 | 1.64 | good | good | good |
| 25 | MAI-5 | EtOH | 22.8 | 54.5 | 22.7 | 17.7 | 48.2 | 34.1 | 69000 | 114000 | 1.66 | good | good | good |
| 26 | MAI-7 | EtOH | 37.0 | 44.5 | 18.5 | 51.2 | 30.1 | 18.7 | 13500 | 47900 | 3.55 | good | good | good |
| 27 | MAI-7 | EtOH | 37.0 | 44.5 | 18.5 | 48.6 | 37.3 | 14.1 | 33200 | 60300 | 1.82 | good | good | good |

TABLE 2-continued

| Syn. Exp. | MAI | solvent | Amount used (wt %) MAI | ① | ② | Component used (wt %) DMS | ① | ② | Molecular weight Mn | Mw | Mw/Mn | Solubility[1] Water[2] | EtOH[3] | Compatibility[4] |
|---|---|---|---|---|---|---|---|---|---|---|---|---|---|---|
| 28 | MAI-7 | EtOH | 37.0 | 44.5 | 18.5 | 39.9 | 44.0 | 16.1 | 33000 | 62100 | 1.88 | good | good | good |

MAI: azo-containing polysiloxane compound
EtOH: ethyl alcohol
①: ethylenically unsaturated carboxylic acid
②: ethylenically unsaturated carboxylic acid ester
② of Example 18: methyl methacrylate
② of Example 19: ethyl methacrylate
② of Example 20: 2-ethylhexyl methacrylate
② of Example 21: stearyl methacrylate
① of Example 22 or 26: acrylic acid
① of Example 23: MAA/itaconic acid (Amount used; 27.3 wt %/27.3 wt %, Component used; 35.3 wt %/8.7 wt %)
① of Example 24: MAA/itaconic acid (Amount used; 49.0 wt %/5.5 wt %, Component used; 49.2 wt %/2.3 wt %)
① of Example 25: MAA/itaconic acid (Amount used; 40.9 wt %/13.6 wt %, Component used; 42.4 wt %/5.8 wt %)
② of Example 22, 23, 24, 25 or 26: BMA
① of Example 18, 19, 20, 21, 27 or 28: MAA
② of Example 27: n-butyl acrylate
② of Example 28: stearyl acrylate
DMS: dimethyl siloxane
Mn: number-average molecular weight
Mw: weight-average molecular weight
Solubility[1]: Judgement was based on transparency of each solution.
water[2]: 2% aqueous solution of the copolymer which is perfectly neutralized with 2-amino-2-methylpropanol.
EtOH[3]: 2% ethanol solution.
compatibility[4]: 2% water/ethanol (50 w/w/50 w/w) solution of the copolymer which is perfectly neutralized with 2-amino-2-methylpropanol.

Example 1

Each of the block copolymers obtained in the above Synthesis Examples is dissolved in ethanol to give 20% solution. Then a solution of 2-amino-2-methyl propanol in a mixture of water and ethanol (50 w/w/50 w/w) is added to the above solution to neutralize the carboxylic acid to 70% degree of neutralization. Purified water is added to the resulting solution so as to adjust the solid resin content to 1 or 2% to give a sample of the base material for hair cosmetics of the present invention.

Comparative test data on evaluation of set-holding ability, curl retention and faking of the samples and conventional base material for hair cosmetics is shown in Table 3.

Feasibility of preparations using the base material for hair cosmetics of the present invention on various kind of evaluation tests is shown in Table 4, and also evaluation of treatment tests is shown in Table 5.

The components and evaluation method of the samples are as described below.

| <Preparation 1> hair lotion for hard set | |
|---|---|
| the block copolymer obtained in Synthesis Example 11 | 2.0 |
| ethanol | 10.0 |
| methyl p-hydroxy benzoate | 0.1 |
| propylene glycol | 1.0 |
| 2-amino-2-methyl propanol | 0.7 |
| polyoxyethylene sorbitan monostearate (20 E.O.) | 0.3 |
| perfume | 0.1 |
| purified water | the rest |
| total | 100.0 |

<Preparation 2> hair mousse for soft set
(undiluted solution)

| the block copolymer obtained in Synthesis Example 11 | 1.0 |
|---|---|
| ethanol | 5.0 |
| methyl p-hydroxy benzoate | 0.1 |
| stearyl trimethyl ammonium chloride | 0.2 |
| glycerine | 1.0 |
| 2-amino-2-methyl propanol | 0.4 |
| silicone emulsion | 1.0 |
| perfume | 0.1 |
| purified water | the rest |
| total | 100.0 |

(spraying solution)

| the undiluted solution | 92.0 |
|---|---|
| liquified petroleum gas | 8.0 |
| total | 100.0 |

<Preparation 3> hair jel for hard set

| the block copolymer obtained in Synthesis Example 4 | 2.0 |
|---|---|
| ethanol | 10.0 |
| methyl p-hydroxy benzoate | 0.1 |
| carboxyvinylpolymer | 0.4 |
| 2-amino-2-methyl propanol | 1.0 |
| polyoxyethylene sorbitan monostearate (20 E.O.) | 0.2 |
| perfume | 0.1 |
| tetrasodium edetate | 0.02 |
| purified water | the rest |
| total | 100.0 |

<Preparation 4> hair mousse for soft set

| the block copolymer obtained in Synthesis Example 8 | 1.0 |
|---|---|
| ethanol | 5.0 |
| methyl p-hydroxybenzoate | 0.1 |
| stearyl trimethyl ammonium chloride | 0.3 |
| POE-modified siloxane | 0.1 |
| 2-amino-2-methyl propanol | 0.27 |
| perfume | 0.1 |
| dibutyl hydroxy toluene | 0.01 |
| purified water | the rest |
| total | 100.0 |

-continued

<Preparation 5> hair mousse for hard set
(undiluted solution)

| | |
|---|---|
| the block copolymer obtained in Synthesis Example 9 | 2.0 |
| ethanol | 10.0 |
| methyl p-hydroxy benzoate | 0.1 |
| 2-amino-2-methyl propanol | 0.46 |
| POE(50) hydrogenated castor oil | 0.3 |
| perfume | 0.1 |
| purified water | the rest |
| total | 100.0 |

(spraying solution)

| | |
|---|---|
| the undiluted solution | 92.0 |
| liquified petroleum gas | 8.0 |
| total | 100.0 |

<Preparation 6> hair mousse for hard set
(undiluted solution)

| | |
|---|---|
| the block copolymer obtained in Synthesis Example 1 | 2.0 |
| ethanol | 10.0 |
| methyl p-hydroxy benzoate | 0.1 |
| 2-amino-2-methyl propanol | 0.4 |
| POE(50) hydrogenated castor oil | 0.3 |
| perfume | 0.1 |
| purified water | the rest |
| total | 100.0 |

(spraying solution)

| | |
|---|---|
| the undiluted solution | 92.0 |
| liquified petroleum gas | 8.0 |
| total | 100.0 |

<Preparation 7> hair lotion for hard set

| | |
|---|---|
| the block copolymer obtained in Synthesis Example 14 | 2.0 |
| ethanol | 10.0 |
| methyl p-hydroxy benzoate | 0.1 |
| 1,3-butylene glycol | 1.0 |
| 2-amino-2-methyl propanol | 0.3 |
| polyoxyethylene sorbitan monostearate (20 E.O.) | 0.3 |
| propylene glycol | 1.0 |
| perfume | 0.1 |
| purified water | the rest |
| total | 100.0 |

<Preparation 8> non-wash-away treatment

| | |
|---|---|
| the block copolymer obtained in Synthesis Example 15 | 2.0 |
| ethanol | 15.0 |
| methyl p-hydroxy benzoate | 0.1 |
| glycerine | 5.0 |
| silicone emulsion | 2.0 |
| 2-amino-2-methyl propanol | 0.33 |
| POE(50) hydrogenated castor oil | 0.3 |
| perfume | 0.1 |
| purified water | the rest |
| total | 100.0 |

<Preparation 9> treatment

| | |
|---|---|
| the block copolymer obtained in Synthesis Example 15 | 10.0 |
| methyl polysiloxane | 5.0 |
| cetanol | 3.0 |
| glyceryl monostearate | 1.0 |
| methyl p-hydroxy benzoate | 0.2 |
| propyl p-hydroxy benzoate | 0.1 |
| glycerine | 5.0 |
| polyoxyethylene sorbitan monostearate (20 E.O.) | 1.0 |
| 2-amino-2-methyl propanol | 0.33 |
| purified water | the rest |
| total | 100.0 |

The evaluation of conventional base materials for hair cosmetics is conducted on water/ethanol (10 w/w/90 w/w) solutions of 1% or 2% solid resin content, respectively.

[Evaluation Test Methods]

1. Set-Holding Ability

The Preparations 1, 3, 4 and 7 obtained above are diluted twice by water, and the undiluted solution of the Preparations 2, 5 and 6 obtained above are diluted three times by water, and the solutions are applied to a swatch of hair, respectively. The thus treated swatches of hair are bended 10 times in total and the flexural rigidities of the swatches after bending once and after bending 10 times and the ratio of the two flexural rigidities is calculated. The obtained values are evaluated on the following standard.

Evaluation Standard

○ - - - >70%

Δ - - - 50–70% x - - - <50%

2. Curl Retention

One ml of each sample (in the Preparations 2, 5 and 6, the undiluted solutions are used) is applied to swatches of hair of each about 2 g in weight and about 30 cm in length, and thus treated swatches of hair are wound around glass tube of 1 cm diameter, followed by drying. The swatches of hair are taken out of the tube and the lengths are measured ($L_0$). Then the swatches of hair are kept under 35° C. and 80 RH % for 2 hours and the length of the curl is measured ($L_2$). The curl retention value is calculated by the following equation on the basis of the measured values, and evaluation is conducted on the basis of the curl retention value by the following evaluation standard.

Curl retention value(%)=$(30-L_2)/(30-L_0) \times 100$.

Evaluation Standard

○ - - - >80%

Δ - - - 60 to 80% x - - - <60%

3. Flaking Test

Each sample is applied or sprayed to swatches of hair, followed by completely drying. Then the swatches of hair are combed and the state of flaking is observed. The evaluation standard is as follows.

○ - - - no flaking is observed

Δ - - - a little flaking is observed x - - - much flaking is observed

4. Sensory Test

About 2 g of each sample is applied or sprayed to swatches of hair of 30 cm length, followed by drying. Thus treated swatches of hair are tested by 5 professional panellers by 5 degree evaluation standard (on a:smoothness of the surface, b:gloss, c:flexibility and d:tackiness), and the average value of the scores (counting fractions of 0.5 and over as a unit and cutting away the rest). The evaluation standard is as follows.

Evaluations Standard 4-a. Smoothness of the Surface degree 5 - - - very smooth degree 4 - - - smooth degree 3 - - - ordinary degree 2 - - - rough degree 1 - - - very rough 4-b. Gloss degree 5 - - - very glossy degree 4 - - - glossy degree 3 - - - ordinary degree 2 - - - not glossy degree 1 - - - extraordinary non-glossy 4-c. Flexibility
- degree 5 - - - flexible
- degree 4 - - - a little flexible
- degree 3 - - - a little flexible but not worried about
- degree 2 - - - little flexible and worried about
- degree 1 - - - not flexible at all 4-d. Tackiness
- degree 5 - - - not tacky at all
- degree 4 - - - little tacky
- degree 3 - - - a little tacky but not worried about
- degree 2 - - - tacky and worried about
- degree 1 - - - very tacky 5. Non-Wash-Away Treatment Test About 2 g of the Preparation 8 obtained above sample is applied to swatches of hair of 30 cm length, followed by drying. Thus treated swatches of hair are tested by 5 professional panellers by 5 degree evaluation standard (on a:smoothness of the surface, b:gloss, c:flexibility and d:tackiness) and the average value of the scores (counting fractions of 0.5 and over as a unit and cutting away the rest). The evaluation standard is as follows.

Evaluations Standard 5-a. Smoothness of the Surface
- degree 5 - - - very smooth
- degree 4 - - - smooth
- degree 3 - - - ordinary
- degree 2 - - - rough
- degree 1 - - - very rough 5-b. Gloss
- degree 5 - - - very glossy
- degree 4 - - - glossy
- degree 3 - - - ordinary
- degree 2 - - - not glossy
- degree 1 - - - extraordinary non-glossy 5-c. Flexibility
- degree 5 - - - flexible
- degree 4 - - - a little flexible
- degree 3 - - - a little flexible but not worried about
- degree 2 - - - little flexible and worried about
- degree 1 - - - not flexible at all 5-d. Tackiness
- degree 5 - - - not tacky at all
- degree 4 - - - little tacky
- degree 3 - - - a little tacky but not worried about
- degree 2 - - - tacky and worried about
- degree 1 - - - very tacky 6. Treatment Test Swatches of hair about 2 g of 30 cm length is dipped into hot water at 40° C. and shampooed by 1.0 wt % aqueous solution of sodium lauryl sulfate, followed by rinsing in hot water at 40° C. for 3 minutes. (1) The Preparation 9 obtained above are applied to thus treated swatches of hair and applicability to hair is evaluated. (2) Next, this swatches of hair are rinsed in hot water at 40° C. for 30 seconds and sliding of swatches of hair is evaluated. (3) After drying, gloss and smoothness are evaluated. Those evaluations are conducted by 5 professional panellers, respectively by 5 degree evaluation standard and the average value of the scores (counting fractions of 0.5 and over as a unit and cutting away the rest). The evaluation standard is as follows.

Evaluations Standard 6-(1). Applicability
- degree 5 - - - very applicable
- degree 4 - - - applicable
- degree 3 - - - ordinary
- degree 2 - - - not applicable
- degree 1 - - - extraordinary non-applicable 6-(2). Sliding for Swatches of Hair
- degree 5 - - - very good sliding
- degree 4 - - - good sliding
- degree 3 - - - ordinary
- degree 2 - - - bad sliding
- degree 1 - - - very bad sliding 6-(3)-1. Gloss
- degree 5 - - - very glossy
- degree 4 - - - glossy
- degree 3 - - - ordinary
- degree 2 - - - not glossy
- degree 1 - - - extraordinary non-glossy 6-(3)-2. Smoothness of the Surface
- degree 5 - - - very smooth
- degree 4 - - - smooth
- degree 3 - - - ordinary
- degree 2 - - - rough
- degree 1 - - - very rough

TABLE 3

A function evaluation Test

| | Synthesis Example No. (neutralization ratio) | general property | | |
|---|---|---|---|---|
| | | set-holding ability | curl retention | flaking |
| The base material for hair cosmetics | Syn. Exp. 11 (70%) | ◯ | ◯ | ◯ |
| | Syn. Exp. 4 (70%) | ◯ | ◯ | ◯ |
| | Syn. Exp. 8 (70%) | Δ | ◯ | ◯ |
| | Syn. Exp. 9 (70%) | ◯ | ◯ | ◯ |
| Conventional base material for hair cosmetics | anion A | Δ | ◯ | Δ |
| | anion B | Δ | ◯ | Δ |
| | anion C | Δ | ◯ | Δ |
| | cation A | Δ | Δ | ◯ |
| | cation B | Δ | ◯ | Δ |
| | amphoteric A | Δ | Δ | ◯ |
| | amphoteric B | Δ | ◯ | Δ |
| | nonion A | Δ | Δ | X |
| | nonion B | Δ | X | Δ |

TABLE 4

Evaluation Test

| preparation | Synthesis Example No. | general property set-holding ability | curl retention | flaking | sensory smoothness | gloss | flexibility | tackiness |
|---|---|---|---|---|---|---|---|---|
| 1 | 11 | ○ | ○ | ○ | 4 | 5 | 4 | 5 |
| 2 | 11 | ○ | Δ | ○ | 5 | 5 | 5 | 5 |
| 3 | 4 | ○ | ○ | ○ | 4 | 5 | 4 | 5 |
| 4 | 8 | Δ | Δ | ○ | 5 | 5 | 5 | 5 |
| 5 | 9 | ○ | ○ | ○ | 4 | 5 | 4 | 5 |
| 6 | 1 | ○ | ○ | ○ | 4 | 5 | 4 | 5 |
| 7 | 14 | ○ | ○ | ○ | 4 | 5 | 4 | 5 |

TABLE 5

Sensory non-wash-away treatment test

| preparation | Syn. Exp No. | smoothness | gloss | flexibility | tackiness |
|---|---|---|---|---|---|
| 8 | 15 | 5 | 5 | 5 | 5 | treatment test

| preparation | Syn. Exp No. | applicability | sliding | gloss | smoothness |
|---|---|---|---|---|---|
| 9 | 15 | 4 | 5 | 5 | 5 |

It is understood from the above that the base material for hair cosmetics of the present invention can give, upon applying to hair, good gloss, good touch and feeling, good combing and causing no stiffness nor tackiness and further that it is clearly excellent in moisture resistance, set-holding ability and anti-flaking ability as compared with conventional base materials for hair cosmetics.

The base material for hair cosmetics of the present invention is, as compared with conventional ones, excellent in moisture resistance, set-holding ability and elasticity and it does not cause flaking and when it applies to hair, natural make-up effect can be given to hair and thus treated hair is flexible and smooth in touch and can smoothly be combed.

What is claimed:

1. A base material for hair cosmetics, which comprises a linear block copolymer comprising 5 to 70% by weight of a polysiloxane segment having a repeating unit of the formula

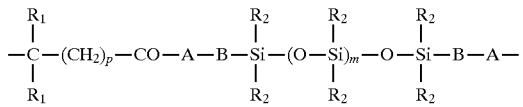

wherein each $R_1$ is hydrogen, lower alkyl or cyano; each $R_2$ is hydrogen, alkyl, haloalkyl or aryl; A is NH or O; B is lower alkylene, oxygen interupted lower alkylene or lower alkenyloxy; p is 0 or an integer of 1 to 6; and m is 0 or an integer of 1 to 200;

10 to 90% by weight of a monomer moiety of an ethylenically unsaturated carboxylic acid having a repeating unit of the formula

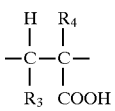

wherein $R_3$ is hydrogen, lower alkyl or carboxyl; and $R_4$ is hydrogen, lower alkyl or lower carboxyalkyl; and 80% or less by weight of a monomer moiety of an ethylenically unsaturated carboxylic acid ester having a repeating unit of the formula

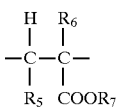

wherein $R_5$ is a hydrogen, lower alkyl or alkoxycarbonyl; and $R_6$ is hydrogen, lower alkyl, lower carboxyalkyl or alkyloxycarbonylalkyl; and $R_7$ is alkyl.

2. The base material for hair cosmetics according to claim 1, wherein the block copolymer has a number-average molecular weight of 60,000 to 150,000.

3. The base material for hair cosmetics according to claim 1, wherein the block copolymer is obtained by polymerizing an ethylenically unsaturated carboxylic acid and an ethylenically unsaturated carboxylic acid ester in the presence of a polyazo group-containing polysiloxane compound.

4. A base material for hair cosmetics, which comprises a block copolymer comprising 5 to 70% by weight of polysiloxane segments having repeating units of the formulas

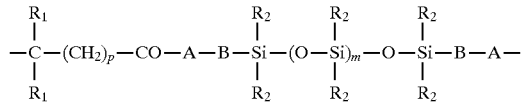

and

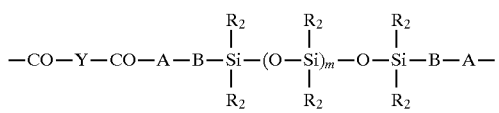

wherein each $R_1$ is hydrogen, lower alkyl or cyano; each $R_2$ is hydrogen, alkyl, haloalkyl or aryl; A is NH or O; B is lower alkylene, oxygen interupted lower alkylene or lower alkenyloxy; p is 0 or an integer of 1 to 6; m is 0 or an integer of 1 to 200; and —CO—Y—CO— is a residue of a dibasic carboxylic acid;

10 to 90% by weight of a monomer moiety of an ethylenically unsaturated carboxylic acid having a repeating unit of the formula

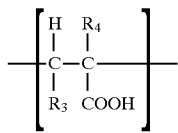

wherein $R_3$ is hydrogen, lower alkyl or carboxyl; and $R_4$ is hydrogen, lower alkyl or lower carboxyalkyl; and 80% or less by weight of a monomer moiety of an ethylenically unsaturated carboxylic acid ester having a repeating unit of the formula

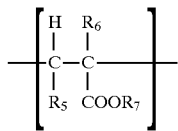

wherein $R_5$ is hydrogen, lower alkyl or alkyloxycarbonyl; $R_6$ is hydrogen lower alkyl, lower carboxyalkyl or alkyloxycarbonylalkyl; and $R_7$ is alkyl.

5. The base material for hair cosmetics according to claim 4, wherein the block copolymer is obtained by polymerizing an ethylenically unsaturated carboxylic acid and an ethylenically unsaturated carboxylic acid ester in the presence of two different polyazo group-containing polysiloxane compounds.

* * * * *